United States Patent [19]

Mota

[11] Patent Number: 5,507,285
[45] Date of Patent: * Apr. 16, 1996

[54] ENDOTRACHEAL TUBE STABILIZER WITH ADHESIVE SECTION

[76] Inventor: Lee H. Mota, 4210 Ticino Valley Dr., Arlington, Tex. 76016

[*] Notice: The portion of the term of this patent subsequent to May 17, 2011, has been disclaimed.

[21] Appl. No.: 168,708

[22] Filed: Dec. 16, 1993

Related U.S. Application Data

[63] Continuation of Ser. No. 656,621, Feb. 19, 1991, Pat. No. Des. 347,059.

[51] Int. Cl.$^6$ .............................. A61M 16/00; A62B 9/06
[52] U.S. Cl. .............................. 128/207.17; 128/DIG. 26; 128/912; 128/207.14
[58] Field of Search .......................... 128/207.14, 207.17, 128/DIG. 26, 911, 912, 200, 26

[56] References Cited

U.S. PATENT DOCUMENTS

| | | | |
|---|---|---|---|
| 3,713,448 | 1/1973 | Arrott | 128/207.17 |
| 4,392,857 | 7/1983 | Beran | 604/179 |
| 4,548,200 | 10/1985 | Wapner | 128/207.17 |
| 4,738,662 | 4/1988 | Kalt et al. | 604/180 |
| 4,838,867 | 6/1989 | Kalt et al. | 604/180 |
| 5,038,778 | 8/1991 | Lott | 128/207.17 |
| 5,219,336 | 6/1993 | Wilk | 604/180 |
| 5,237,988 | 8/1993 | McNeese | 128/207.17 |
| 5,292,312 | 3/1994 | Delk et al. | 604/180 |

FOREIGN PATENT DOCUMENTS 2251796  7/1992  United Kingdom ........... 128/DIG. 26

OTHER PUBLICATIONS

"On the Market" advertising brochure, advertising ET Tube Stabilizer, *JEMS*, Atem Enterprises, Denton, TX 76202, (817)383-3266.

*Primary Examiner*—Kimberly L. Asher
*Attorney, Agent, or Firm*—Fulbright & Jaworski

[57] ABSTRACT

An endotracheal tube stabilizer includes a central z-shaped body portion including a generally rectangular portion and offset portions extending leftwardly and rightwardly therefrom to define a "z" shape. Strap members extend from the ends of the offsets and are used to secure the endotracheal tube stabilizer on the patient. The z-shaped portion has an adhesive layer on one side thereof, the adhesive layer preferably protected by a backing layer that is removed prior to use. In use, the backing layer is removed and the z-shaped of the endotracheal tube stabilizer is attached to an endotracheal tube. The strap members are then secured to the patient to hold the endotracheal tube in place.

3 Claims, 2 Drawing Sheets

5,507,285

ENDOTRACHEAL TUBE STABILIZER WITH ADHESIVE SECTION

This Application is a continuation of application Ser. No. 656,621, filed Feb. 19, 1991, now U.S. Design Patent No. D 347,059.

TECHNICAL FIELD OF THE INVENTION

This invention relates generally to endotracheal tube stabilizers.

BACKGROUND AND SUMMARY OF THE INVENTION

Previously, endotracheal tubes have been stabilized in the mouth of a patient utilizing adhesive tape. This procedure is generally unsatisfactory because the tape causes unwanted and unnecessary irritation to the skin. Additionally, in an emergency situation, adhesive tape may be difficult to locate and apply.

Prior attempts at rectifying the difficulties of stabilizing endotracheal tubes with adhesive tape are addressed in the following U.S. Pat. Nos. 3,161,199; 3,713,448; 3,927,676; 4,223,671; 4,270,529; 4,326,515; 4,329,984; 4,331,143; 4,378,012; 4,449,527; 4,774,944; 4,832,019; 4,844,061; and 4,867,154.

In general, the endotracheal tube stabilizers comprising the subject matters of the above-listed patents have been unduly complicated, and therefore, expensive to manufacture and difficult to use.

The present invention comprises an endotracheal tube stabilizer which overcomes the foregoing and other difficulties long since associated with the prior art. In accordance with the broader aspects of the invention, an endotracheal tube stabilizer comprises a central z-shaped body portion including a generally rectangular portion and two offset portions, one extending leftwardly and the other extending rightwardly from the rectangular portion to define a "z" shape. Straps extend outwardly from the offset portions. The z-shaped portion is provided with adhesive on one side thereof, with a backing layer protecting the adhesive prior to use.

In the use of the endotracheal tube stabilizer of the present invention, the backing layer overlying the adhesive is removed, and the z-shaped portion is attached to the endotracheal tube. The straps emanating from the z-shaped portion are then positioned in place.

DESCRIPTION OF THE DRAWINGS

A more complete understanding of the invention may be had by reference to the following Detailed Description when taken in conjunction with the accompanying drawings wherein.

DETAILED DESCRIPTION

Figure 1:
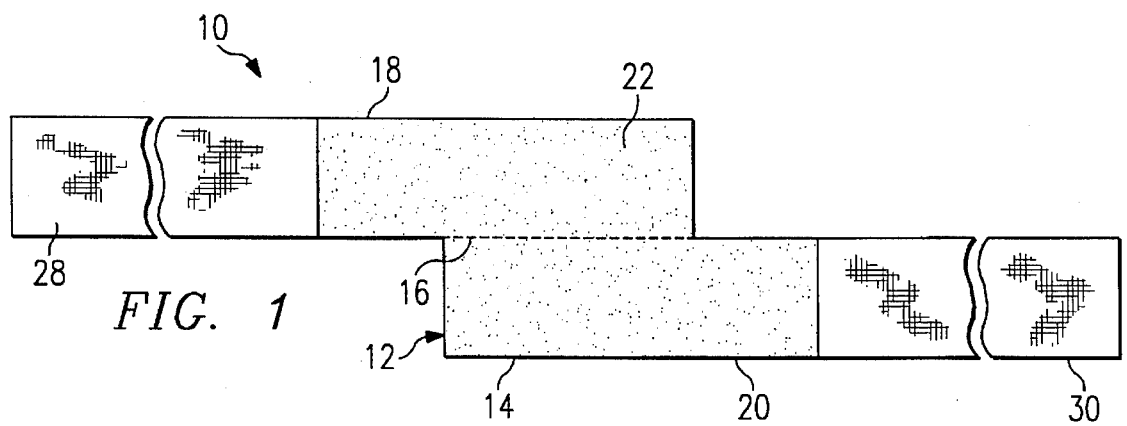
FIG. 1 is a front view of an endotracheal tube stabilizer incorporating the preferred embodiment of the invention.

Referring now to the drawings, and particularly to FIG. 1 thereof, there is shown an endotracheal tube stabilizer 10 comprising the preferred embodiment of the invention. The endotracheal tube stabilizer 10 is a substantially continuous planar member, and includes a central z-shaped portion 12 having an internally rectangular portion 14 at the center thereof. An axis 16 divides the rectangular portion 14 into upper and lower segments. A first extension 18 extends leftwardly from the upper segment of the rectangular portion 14, and a second extension 20 extends rightwardly from the lower segment of the rectangular portion 14. An adhesive layer 22 is applied to one planar surface of the z-shaped portion 12, whereas, as can be seen on FIG. 2, the other planar surface remains free of adhesive.

A first strap 28 extends from the first extension 18, and a second strap 30 extends from the second extension 20.

Figure 7:
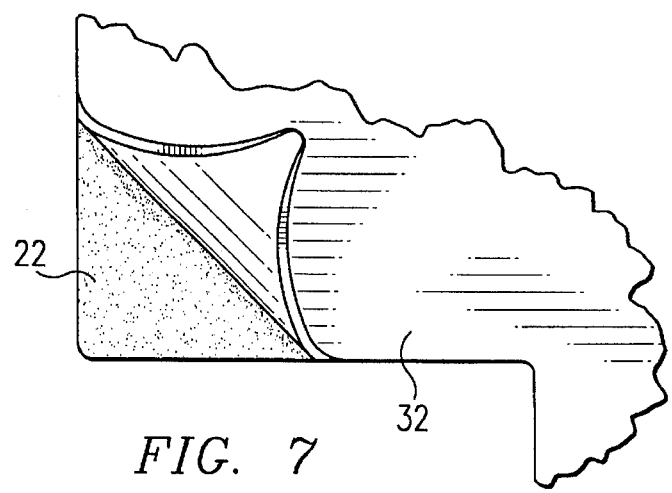
FIG. 7 is an illustration of the adhesive and peel away section of the apparatus of FIG. 1.

Referring now to FIG. 7, a backing layer 32 normally overlies the adhesive layer 22 on the z-shaped portion 12 of the endotracheal tube stabilizer 10. The backing layer 32 is removed prior to use.

Figure 8:
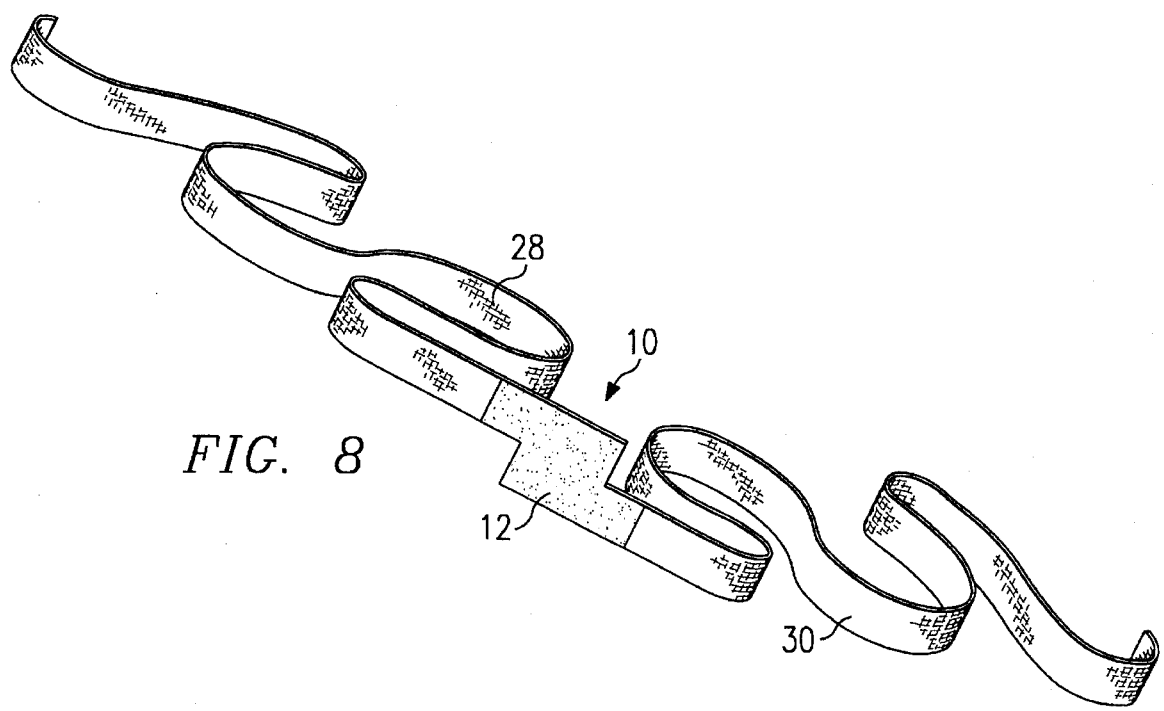
FIG. 8 is a front perspective view of the apparatus of FIG. 1.

FIG. 8 demonstrates the relative proportions between the body portion 12 and the straps 28 and 30 of the endotracheal tube stabilizer 10. The offset relationship between the straps 28 and 30 as extending from the extensions 18 and 20 of the z-shaped portion 12 comprises an essential feature of the invention.

Although the preferred embodiments of the invention have been illustrated and the accompanying drawings are described in the foregoing Detailed Description, it will be understood that the apparatus of the present invention is capable of numerous rearrangements, modification and variations of the parts and elements thereof without departing from the spirit of the invention.

Figure 2:
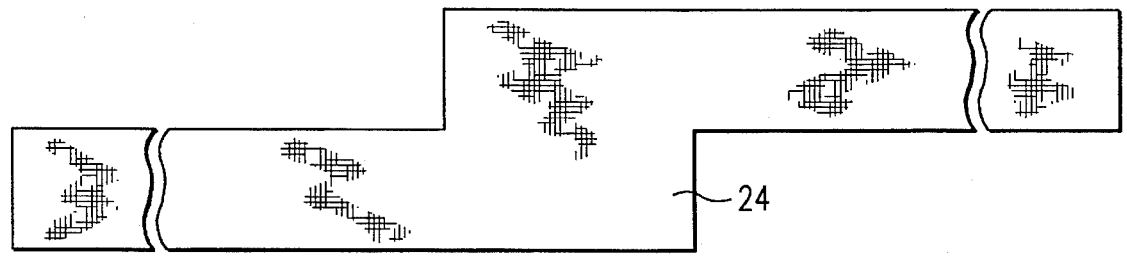
FIG. 2 is a back view of the apparatus of FIG. 1.
Figure 3:
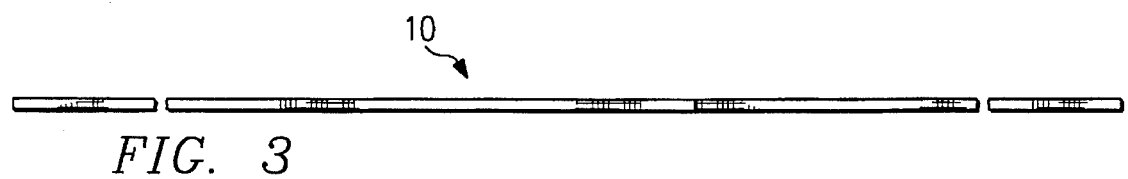
FIG. 3 is a right side view of the apparatus of FIG. 1.
Figure 4:
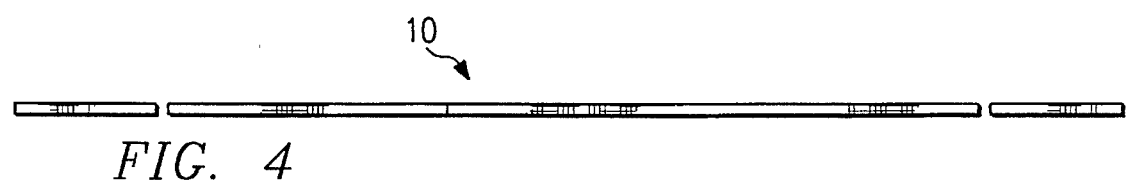
FIG. 4 is a left side view of the apparatus of FIG. 1.
Figure 5:
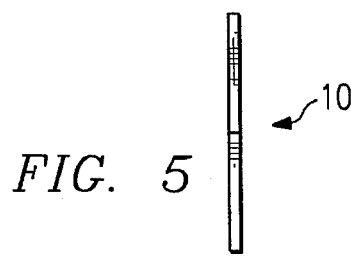
FIG. 5 is a top view of the apparatus of FIG. 1.
Figure 6:
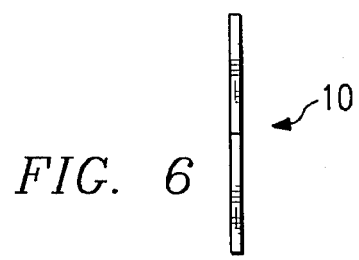
FIG. 6 is a bottom view of the apparatus of FIG. 1.

I claim:

1. An endotracheal tube stabilizer, comprising:

a substantially continuous planar member, the planar member having an averse and a reverse side, the planar member also having a central portion, the central portion divided into a lower segment and an upper segment by a transverse axis drawn therethrough;

a left extension of the central portion and a right extension of the central portion, the left extension extending leftwardly from the upper segment of the central portion and the right extension extending rightwardly from the lower segment of the central portion, the left extension and the central portion and the right extension defining a z-shaped portion as shown on FIGS. 1 and 2;

a left strap means and a right strap means, the left strap means extending leftwardly from the left extension and the right strap means extending rightwardly from the right extension;

a contact adhesive, the contact adhesive provided on the averse side only of an area defined by the z-shaped portion; and a backing layer, the backing layer covering the contact adhesive and protecting the contact adhesive from unwanted premature contact, the backing layer also susceptible to being peeled off to expose the contact adhesive when contact is eventually desired.

2. An endotracheal tube stabilizer, comprising:

a substantially continuous planar member, the planar member having an averse and a reverse side, the planar member also having a central portion, the central portion divided into a lower segment and an upper segment by a transverse axis drawn therethrough;

a left extension of the central portion and a right extension of the central portion, the left extension extending leftwardly from the upper segment of the central portion and the right extension extending rightwardly from the lower segment of the central portion, the left extension and the central portion and the right extension defining a z-shaped portion as shown on FIGS. 1 and 2; and a left strap means and a right strap means, the left strap means extending leftwardly from the left extension and the right strap means extending rightwardly from the right extension.

3. The endotracheal tube of claim 2, further comprising:

a contact adhesive, the contact adhesive provided on the averse side only of an area defined by the z-shaped portion; and a backing layer, the backing layer covering the contact adhesive and protecting the contact adhesive from unwanted premature contact, the backing layer also susceptible to being peeled off to expose the contact adhesive when contact is eventually desired.

* * * * *